US010424412B2

(12) United States Patent
Huang (10) Patent No.: US 10,424,412 B2
(45) Date of Patent: Sep. 24, 2019

(54) PRIVACY-CONTROLLED CARE REQUESTER COMMUNICATION SYSTEM WITH ON-DEMAND CAREGIVER CONFERENCING AND REAL-TIME VITAL STATISTICS ALERT

(71) Applicant: Jeffrey Huang, San Jose, CA (US)

(72) Inventor: Jeffrey Huang, San Jose, CA (US)

(*) Notice: Subject to any disclaimer, the term of this patent is extended or adjusted under 35 U.S.C. 154(b) by 0 days.

(21) Appl. No.: 15/885,748

(22) Filed: Jan. 31, 2018

(65) Prior Publication Data

US 2019/0237204 A1 Aug. 1, 2019

(51) Int. Cl.
*G16H 80/00* (2018.01)
*H04W 12/02* (2009.01)
*G08B 25/01* (2006.01)
*H04N 7/15* (2006.01)
*H04N 7/18* (2006.01)

(52) U.S. Cl.
CPC .......... *G16H 80/00* (2018.01); *G08B 25/016* (2013.01); *H04N 7/155* (2013.01); *H04N 7/183* (2013.01); *H04W 12/02* (2013.01)

(58) Field of Classification Search
USPC ...................................... 379/37–52
See application file for complete search history.

(56) References Cited

U.S. PATENT DOCUMENTS

| 8,209,195 | B2* | 6/2012 | Dicks ................... A61B 5/0022 705/2 |
| 2003/0012344 | A1* | 1/2003 | Agarwal ................. H04M 11/04 379/37 |
| 2003/0069752 | A1* | 4/2003 | LeDain ................ G06F 19/3418 705/2 |
| 2015/0081338 | A1* | 3/2015 | Lai .......................... G06Q 50/22 705/3 |
| 2016/0161985 | A1* | 6/2016 | Zhang ..................... G06F 1/163 361/679.03 |
| 2017/0242428 | A1* | 8/2017 | Pal ........................... H04W 4/90 |
| 2018/0211059 | A1* | 7/2018 | Aunger ............... G06F 21/6263 |
| 2018/0376156 | A1* | 12/2018 | Deshpande ........ H04N 21/8358 |

* cited by examiner

*Primary Examiner* — Maria El-Zoobi
(74) *Attorney, Agent, or Firm* — Invent Capture, LLC.; Samuel S. Cho (57) ABSTRACT

A privacy-controlled care requester communication system includes a care-requester onsite monitoring and communication device and a cloud-computing server accommodating on-demand caregiver conferencing and vital stat alert capabilities. The care-requester onsite monitoring and communication device provides a closed-circuit visual and audio monitoring of the care requester's vicinity with specialized privacy permission rules that are set and adjusted by the care requester to achieve a personally-comfortable balance between health/safety risk monitoring and privacy considerations for a grownup patient. The care-requester onsite monitoring and communication device also enables either the care requester or the caregiving entity to initiate a "welfare check" webcam conferencing using the same care-requester onsite monitoring and communication device. Optionally, the privacy-controlled care requester communication system incorporates a care requester emergency bell device, a care requester wearable device, and environmental and/or vital sensors that can remotely measure the care requester's vital signs and environmental risk factors.

12 Claims, 6 Drawing Sheets

100

A Care-Requester Onsite Monitoring and Communication Device Connected to a Privacy-Controlled Care Requester Communication System

A Care-Requester Onsite Monitoring and Communication Device Connected to a Privacy-Controlled Care Requester Communication System

FIG. 1

A System Block Diagram Example of a Care-Requester Onsite Monitoring and Communication Device

FIG. 2

Privacy-Controlled Care Requester Communication System with On-Demand Caregiver Conferencing and Real-Time Vital Statistics Alert

Logical Component Block Diagram for a Privacy-Controlled Care Requester Communication System

FIG. 5

An Operational Flowchart for a Privacy-Controlled Care Requester Communication System with On-Demand Caregiver Conferencing and Vital Stat Alert

FIG. 6

PRIVACY-CONTROLLED CARE REQUESTER COMMUNICATION SYSTEM WITH ON-DEMAND CAREGIVER CONFERENCING AND REAL-TIME VITAL STATISTICS ALERT

BACKGROUND OF THE INVENTION

The present invention generally relates to safety monitoring and health risk alert communication devices. The present invention also relates to senior or patient care monitoring, health risk alert generation, and on-demand multimedia communication between a care requester and a caregiver. In addition, the present invention also relates to a novel onsite monitoring and communication device connected to cloud-computing resources for effective monitoring and care of a care requester. Furthermore, the present invention also relates to an emergency bell device and/or an environmental or vital sensor that can proactively identify and communicate a care requester's health or safety risks to a caregiver through the cloud-computing resources. Moreover, the present invention also relates to empowering a care requester various levels of privacy permission settings for safety monitoring and health risk alert communication between a care requester and a caregiver at a comfort level of privacy personally configured by the care requester.

Senior patient care and monitoring needs are increasingly becoming important and challenging aspects of healthcare services, especially in developed countries where the median age of the general population is rapidly shifting upward due to increased life expectancy of senior citizens. Furthermore, general social, cultural, and economic changes in family relationships are also bringing dramatic changes to senior patient care needs, as grownup children often live farther away and separately from their senior parents compared to their previous generational counterparts. In today's society, grownup children or other younger members of the family face significant challenges in accommodating and responding to urgent senior care needs in case of emergencies or accidents experienced by senior members of the family.

Moreover, regardless of one's age, a disabled patient or another care requester, who may benefit from meticulous health and safety monitoring by a caregiver, faces significant challenges in receiving appropriate levels of care and supervision, especially if the caregiver is not always physically present in the vicinity of the care requester. Even though the care requester may utilize conventional methods of communication, such as phone calls, text messages, and emails, to inform a remotely-located caregiver his or her urgent need in an event of an emergency or an accident, physical deterioration and related challenges that are prevalent among senior or disabled patients may prevent or hamper the care requester from communicating timely alert(s) to the caregiver.

Conventional devices that attempted to resolve unique challenges faced by seniors and disabled patients include a "baby monitoring" device, which functions as a closed-circuit security camera that transmits video and/or audio feeds from the location of the baby monitoring device to a destination electronic device, such as a PC, a notebook computer, or a smart phone. However, as the name "baby monitoring" device suggests, such security camera devices are merely capable of passively transmitting video and/or audio feeds captured from their fields of view from camera lenses, and do not empower a care requester from actively communicating with the caregiver.

Other conventional senior care devices include an emergency bell button device and a wearable electronic device that allow a care requester to reach an emergency call center when an emergency button is triggered. However, these conventional devices fail to empower the care requester from describing or showing what a particular risk or an urgent care need that the care requester is experiencing at the moment of the emergency button press, if the care requester is unable to speak or verbalize his or her emergency needs.

Furthermore, conventional baby monitor-style security camera devices introduce additional challenges in privacy violations in everyday life of a care requester, especially if the care requester is an adult who is not cognitively impaired and is not under legal guardianship of another individual. For example, a senior citizen (i.e. an adult care requester) may feel uncomfortable in placing a baby monitoring device in a bedroom due to privacy issues. Even if the caregiver was the senior citizen's grownup child who agreed to monitor his or her parent through the baby monitor for the parent's likely medical need in the near future, the senior citizen, who is not cognitively impaired, may desire certain assurances of privacy, depending on the time of the day or specific situations that require privacy.

Therefore, it may be desirable to devise a novel patient care electronic system that provides privacy level-adjustable onsite monitoring as well as two-way communication capabilities between a care requester and a care giver. Moreover, it may also be desirable to devise a novel patient care electronic system that incorporates a dedicated onsite monitoring device that provides dual functionalities of privacy level-adjustable patient security monitoring and on-demand webcam conferencing.

In addition, it may also be desirable to devise a novel patient care electronic system that also incorporates one or more emergency bell devices, patient vital sensors, environmental sensors, and patient-wearable devices that enable the novel patient care electronic system to produce autonomous machine-generated decisions in creating patient endangerment alerts to electronic devices accessed by caregivers for efficient and timely patient care management. Furthermore, it may also be desirable to devise a method of operating a novel privacy-controlled patient care electronic system that provides remote yet timely and proactive monitoring of care requesters who may encounter sudden health or safety endangerments.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

In one embodiment of the invention, a privacy-controlled care requester communication system is disclosed. This privacy-controlled care requester communication system comprises: a care-requester onsite monitoring and communication device that provides dual capabilities of a closed-circuit visual and audio monitoring of a care requester and an on-demand welfare check videoconferencing initiated by a caregiving entity; a cloud-computing server incorporating a care requester's privacy control module, an analytical and alert threshold determination module for identifying imminent health risk to the care requester from the closed-circuit visual and audio monitoring, an on-demand welfare check videoconferencing module, and a care requester endangerment alert module, which are executed in a CPU and a memory unit of the cloud-computing server to operate the privacy-controlled care requester communication system; a care requester's privacy control and permission rules interface generated by the care requester's privacy control module, which allows the care requester to adjust a transmission or access privilege for the closed-circuit visual and audio monitoring during a particular event or a particular timeframe of a day or a week to protect the care requester's privacy by preventing the caregiving entity from eavesdropping through the care-requester onsite monitoring and communication device, when the care requester desires extra privacy during the particular event or the particular timeframe of the day or the week; and a data network operatively connecting the care-requester onsite monitoring and communication device and the cloud-computing server incorporating the care requester's privacy control module, the analytical and alert threshold determination module for identifying imminent health risk to the care requester from the closed-circuit visual and audio monitoring, the on-demand welfare check videoconferencing module, and the care requester endangerment alert module.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble one or more care requester communication systems with on-demand caregiver conferencing and real-time vital statistics alert and any methods of operating thereof. These descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention do not inherently indicate any particular order nor imply any limitations in the invention.

For the purpose of describing the invention, a "vital sensor" is defined as a human vital sign measurement device, which may detect, determine, and/or measure heart rates, electrocardiograms, blood pressures, body temperatures, blood sugar levels, or another physiological sign from a care requester.

In addition, for the purpose of describing the invention, an "environmental sensor" is defined as a sensing apparatus that can detect one or more conditions near a current location of the sensing apparatus. An environmental sensor may detect temperature, humidity levels, ambient noise levels, brightness levels, or ambient gas concentrations in the air. Therefore, a thermometer, a humidity sensor, a microphone, a photo intensity sensor, and a gas sensor (e.g. oxygen, carbon monoxide, carbon dioxide, and etc.) are examples of environmental sensors.

Furthermore, for the purpose of describing the invention, a "care requester" is defined as a person who desires and/or necessitates health monitoring and close communication with another entity (e.g. a family number, an assigned nurse, an assigned doctor, etc.) due to the person's age, physical, and/or medication conditions. For example, a care requester may be a senior citizen, a disabled patient, or a patient with a potentially-dangerous medical condition.

In addition, for the purpose of describing the invention, a "caregiver" is defined as a person (e.g. a grownup child of a care requester, another family member, a designated nurse, etc.) or an entity (e.g. a hospital, a corporation, or another organization) responsible for monitoring and communicating with the care requester. The caregiver may be the first person or the first entity to be alerted in case of an emergency or an urgent need necessitating immediate attention One aspect of an embodiment of the present invention is providing a privacy-controlled care requester communication system that provides privacy level-adjustable onsite monitoring as well as two-way communication capabilities between a care requester and a caregiver.

Furthermore, another aspect of an embodiment of the present invention is providing a privacy-controlled care requester communication system that incorporates a dedicated onsite monitoring device that provides dual functionalities of privacy level-adjustable patient security monitoring and on-demand webcam conferencing.

In addition, another aspect of an embodiment of the present invention is providing a privacy-controlled care requester communication system that also incorporates one or more emergency bell devices, patient vital sensors, environmental sensors, and patient-wearable devices that enable the privacy-controlled care requester communication system to produce autonomous machine-generated decisions in creating patient endangerment alerts to electronic devices accessed by caregivers for efficient and timely patient care management.

Yet another aspect of an embodiment of the present invention is providing a method of operating a privacy-controlled care requester communication system that provides remote yet timely and proactive monitoring of care requesters who may encounter sudden health or safety endangerments.

Figure 1:
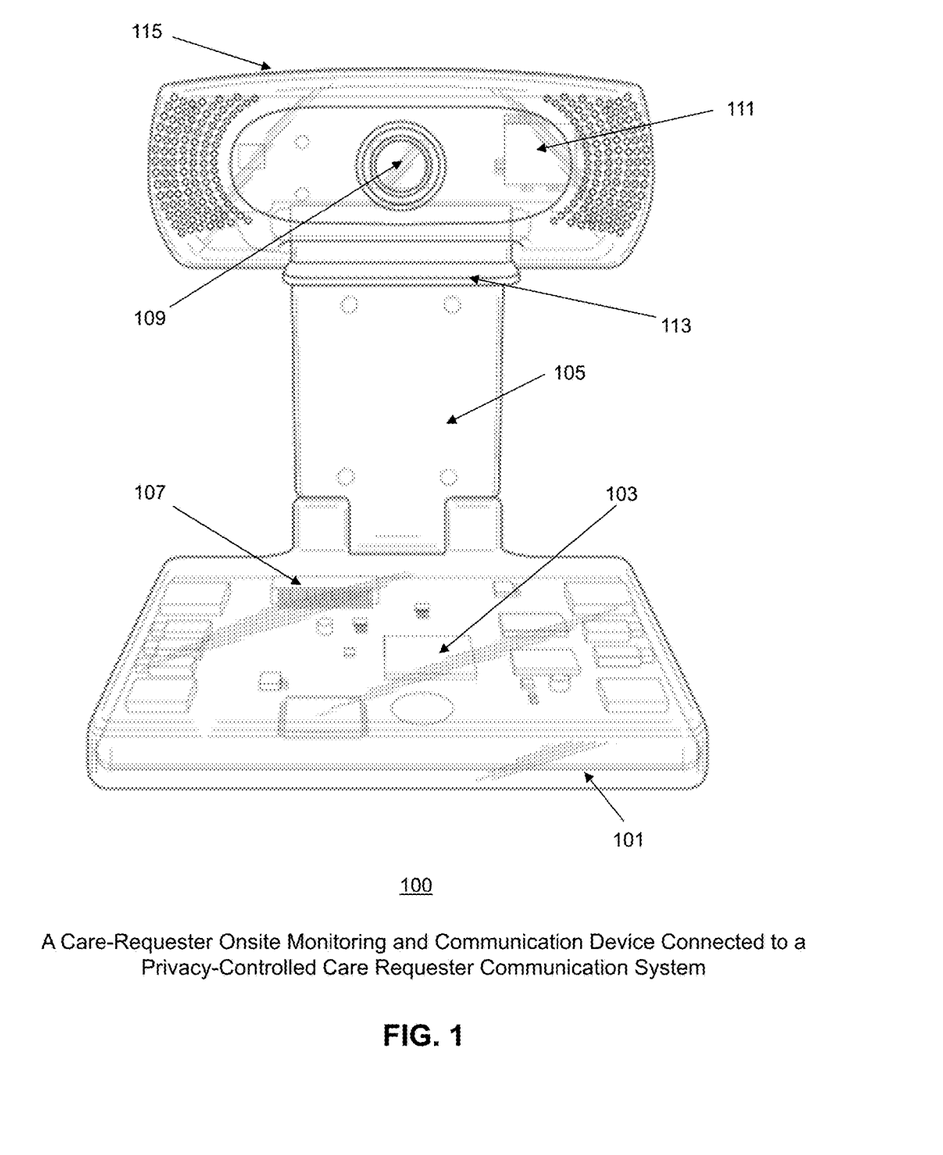
FIG. 1 shows an embodiment of a care-requester onsite monitoring and communication device connected to a privacy-controlled care requester communication system with on-demand caregiver conferencing and real-time vital statistics alert, in accordance with an embodiment of the invention.

FIG. 1 shows an embodiment of a care-requester onsite monitoring and communication device (100) connected to a privacy-controlled care requester communication system with on-demand caregiver conferencing and real-time vital statistics alert, in accordance with an embodiment of the invention. In this embodiment, the care-requester onsite monitoring and communication device (100) incorporates distributed circuit casings (101, 115) and a neck structure (105), which may encapsulate communication cables between the distributed circuit casings (101, 115). In another embodiment, the care-requester onsite monitoring and communication device (100) may be encapsulated in a singular body structure where all circuits are incorporated into one casing.

The care-requester onsite monitoring and communication device (100) is configured to provide webcam conferencing capabilities between a care requester and a caregiver, which may be initiated by either party with an emergency button press located on the care-requester onsite monitoring and communication device, on a separate emergency bell device (e.g. 301, 303 in FIG. 3), or on a patient-wearable device (e.g. 307 in FIG. 3) that are operatively connected to the care-requester onsite monitoring and communication device (100) and the privacy-controlled care requester communication system. The web conferencing from the care-requester onsite monitoring and communication device (100) may also be initiated by a computerized user interface accessible on a care requester's personal computer, a notebook computer, a tablet computer, or a smart phone, which can be connected to the care-requester onsite monitoring and communication device (100) by wireless LAN or the Internet.

Importantly, in the embodiment of the invention as shown in FIG. 1, the care-requester onsite monitoring and communication device (100) also provides intelligent visual and audio patient (i.e. care requester) monitoring within the constraints of care requester-specified privacy controls. For example, if the care requester does not want to give visual and audio monitoring access to a caregiver during a friend's visit to the care requester's residence between 2 p.m. and 4 p.m. tomorrow, then the care requester can set and reserve the privacy settings to exclude visual and audio monitoring between the hours during the friend's visit. Similarly, if the care requester is about to change cloths and does not want the caregiver to have access to visual monitoring footage, the care requester may adjust privacy settings or press a hot button, if any, on the care-requester onsite monitoring and communication device (100) to exclude video monitoring feed transmission to a cloud server in order to protect his or her privacy during the clothing change.

The care requester may also selectively choose video, audio, environmental, or real-time vital statistics information gathered from the care-requester onsite monitoring and communication device (100) and vital sensors for privacy filtering in data sharing or blocking decisions, based on the care requester's particular privacy preferences during the course of health and safety monitoring. Preferably, the caregiver is still able to initiate video conferencing with the care requester and may also be empowered with privacy setting override privileges, if a particular situation is urgent for the safety of the care requester. In the event of a privacy setting override, it is preferable to implement an automated aural and/or visual message to the care requester via the care-requester onsite monitoring and communication device (100) to indicate transparently that the privacy settings are currently being circumvented due to emergency needs of the care requester.

Continuing with the embodiment of the invention as shown in FIG. 1, the care-requester onsite monitoring and communication device (100) comprises a swivel-capable bottom housing (101) and a swivel-capable top housing (115) that form the distributed circuit casing (101, 115), plus the cable-encapsulating neck structure (105). In the preferred embodiment, the swivel-capable bottom housing (101) contains a network communication-capable computing circuitry (103), which comprises a CPU, a memory unit, a camera data interface, and an external data communication interface (107). In addition, the swivel-capable bottom housing (101) may also contain a local data storage, a graphics unit (e.g. a graphics processor unit, a display driver, and etc.), and a power management unit. Preferably, the power management unit of the swivel-capable bottom housing (101) is operatively connected to a power source, such as a power outlet, a power adapter, and/or a battery unit. Furthermore, in the preferred embodiment of the invention, the swivel-capable top housing (115) contains a patient monitoring webcam camera circuitry (111), which comprises a camera lens (109), a camera processing unit (e.g. 215 of FIG. 2), and/or a patient monitoring webcam unit interface.

Moreover, as shown in one embodiment of the invention in FIG. 1, the cable-encapsulating neck structure (105) is interposed between the swivel-capable bottom housing (101) and the swivel-capable top housing (115). In addition, the cable-encapsulating neck structure (105) may also include a webcam hanger (113) that protrudes from a frontal edge of the cable-encapsulating neck structure (105). In another embodiment of the invention, the care-requester onsite monitoring and communication device (100) may simply be incorporated into a singular casing without the cable-encapsulating neck structure (105). The care-requester onsite monitoring and communication device (100) is a novel patient-monitoring device that provides two-way and on-demand caregiver conferencing capabilities (i.e. for emergency communications and general video conferencing needs), while also functioning primarily as a closed-circuit patient monitoring device with unique privacy controls to empower the care requester with a comfortable and personalized balance between privacy needs and patient safety and health monitoring needs. Furthermore, in some embodiments of the invention, the care-requester onsite monitoring and communication device (100) may also function as an Internet modem and a general-purpose cloud network-connected computing device for web browsing, if a separate display screen or a television screen is connected to the care-requester onsite monitoring and communication device (100).

Figure 2:
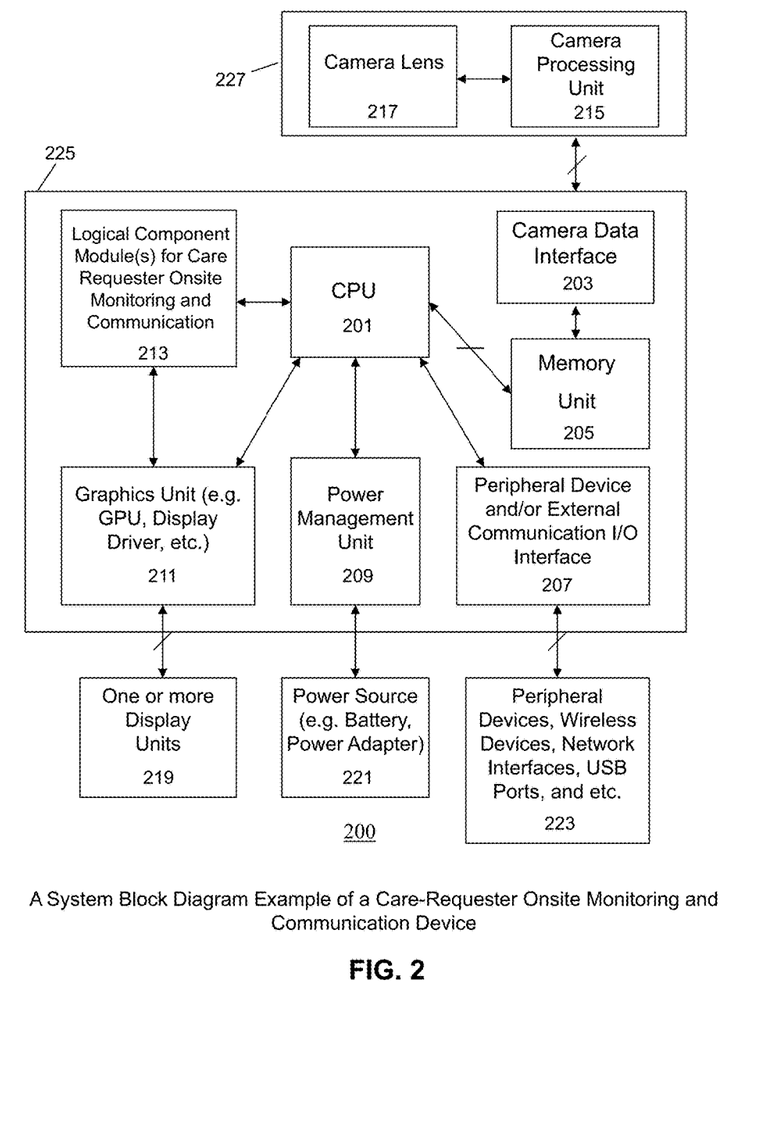
FIG. 2 shows a system block diagram example of a care-requester onsite monitoring and communication device with on-demand caregiver conferencing and real-time vital statistics alert, in accordance with an embodiment of the invention.

FIG. 2 shows a system block diagram example (200) of a care-requester onsite monitoring and communication device with on-demand caregiver conferencing and real-time vital statistics alert, in accordance with an embodiment of the invention. The system block diagram example (200) in FIG.

2 illustrates logical units contained in the care-requester onsite monitoring and communication device in distributed circuit casings (i.e. 225, 227) and an elongated neck structure, in accordance with an embodiment of the invention. In a preferred embodiment of the invention, the care-requester onsite monitoring and communication device is capable of capturing raw patient visual and audio monitoring data and any other multimedia data via a camera lens (217), processing and transforming the raw patient visual and audio monitoring data into a standardized multimedia data set, and transmitting the standardized multimedia data set to a cloud network using a wireless transceiver or a wired network modem embedded in the care-requester onsite monitoring and communication device.

As shown in FIG. 2, in one embodiment of the invention, a network communication-capable computing circuitry (225) comprises a CPU (201), a camera data interface (203), a memory unit (205), a peripheral device and/or external communication input/output interface (207), a power management unit (209), a graphics unit (211), and a logical component module for care requester onsite monitoring and communication (213). At a minimum, the network communication-capable computing circuitry (225) in a first housing (e.g. a bottom housing) is configured to transmit patient visual and audio monitoring data received from the camera data interface (203) to another electronic device accessed by a caregiver via a data network, which may be a wireless data network, a wired data network, or a combination of the two networks.

Preferably, the network communication-capable computing circuitry (225) also performs more tasks than the data transmission function alone. For example, the network communication-capable computing circuitry (225) can first receive raw multimedia data captured from a camera lens (217) and a camera processing unit (215) of a patient monitoring camera-specific circuitry (227) in a second housing (e.g. a top housing). In one embodiment of the invention, the camera processing unit (215) is capable to activating or deactivating the camera lens (217) based on commands received from the CPU (201) in the network communication-capable computing circuitry (225). The camera processing unit (215) may also supply electrical power to the camera lens (217). The camera processing unit (215) may also provide some level of preliminary processing of raw multimedia data captured from the camera lens (217). Examples of preliminary processing of raw multimedia data include image noise filtering, noise suppression, and other beneficial real-time adjustments. The network communication-capable computing circuitry (225) and its CPU (201) can then further process and transform the raw multimedia data into processed multimedia data in a standardized format, such as JPEG or MPEG.

Furthermore, in the preferred embodiment of the invention, the data communication between the first housing that contains the network communication-capable computing circuitry (225) and the second housing that contains the patient monitoring camera-specific circuitry (227) is provided by a data communication and power cable, which is encased inside a cable-encapsulating neck structure (e.g. 105 of FIG. 1) interposed between the first housing and the second housing for the care-requester onsite monitoring and communication device. The complete encapsulation of the data communication and power cable without any freely-hanging exposed portion of data cables between the first housing and the second housing is made possible by utilizing the cable-encapsulating neck structure (e.g. 105 of FIG. 1) that embodies a unique and novel multi-segment casing design for the care-requester onsite monitoring and communication device, in accordance with one or more embodiments of the invention. In another embodiment of the invention, the network communication-capable computing circuitry (225) and the patient monitoring camera-specific circuitry (227) are incorporated into a single case without utilizing the cable-encapsulating neck structure of the preferred embodiment.

Continuing with the embodiment of the invention as shown in FIG. 2, the network communication-capable computing circuitry (225) contains a plurality of logical units, such as the CPU (201), the camera data interface (203), the memory unit (205), the peripheral device and/or external communication I/O interface (207), the power management unit (209), the graphics unit (211), and the logical component module (213) for care requester onsite monitoring and communication. These logical units may be placed on a single printed circuit board in one embodiment of the invention, or on a plurality of printed circuit boards in another embodiment of the invention. Moreover, in one embodiment, the logical component module (213) for care requester onsite monitoring and communication incorporates one or more datasets and logical units as shown and described in FIG. 4. In one embodiment, the logical components for care requester onsite monitoring and communication are software-implemented components stored in a non-volatile data storage medium. In another embodiment, these logical components are hard-coded into an application-specific semiconductor chip as a specialized hardware unit. Yet in another embodiment, some logical components may be retrieved and executed as software modules while other logical components are executed in an application-specific semiconductor chip integrated into the care-requester onsite monitoring and communication device.

Furthermore, in a preferred embodiment of the invention, the CPU (201) is configured to control each logical unit operatively (i.e. directly or indirectly) connected to the CPU (201). The memory unit (205) typically comprises volatile memory banks based on DRAM's. In some embodiments of the invention, the memory unit (205) may use non-volatile memory technologies such as SRAM's and/or Flash memory. The memory unit (205) is capable of storing or uploading programs and applications which can be executed by the CPU (201), the graphics unit (211), or another logical unit operatively connected to the memory unit (205). In one or more embodiments of the invention, software components that provide data transformations and conversions from raw multimedia data to processed multimedia data in a standardized format, for example, may be stored in a local data storage and then can be executed on the CPU (201) and the memory unit (205) of the care-requester onsite monitoring and communication device as needed.

In addition, as shown in FIG. 2, the peripheral device and/or external communication I/O interface (207) may be operatively connected to a wireless transceiver and an radio frequency (RF) antenna for wireless data access via a cloud network. The peripheral device and/or external communication I/O interface (207) can also be operatively connected to a plurality of electronic devices via a data network and/or a direct device-to-device connection method. Moreover, the power management unit (209) is operatively connected to a power supply unit and a power source (e.g. battery, power adapter) (221), and the power management unit (209) generally controls power supplied to various logical units in the care-requester onsite monitoring and communication device. Furthermore, in one embodiment of the invention, the graphics unit (211) in the system block diagram (200)

comprises a graphics processor, a display driver, a dedicated graphics memory unit, and/or another graphics-related logical components. In general, the graphics unit (211) is able to process and communicate graphics-related data with the CPU (201), the display driver, and/or the dedicated graphics memory unit. The graphics unit (211) is also operatively connected to one or more display units (219).

Figure 3:
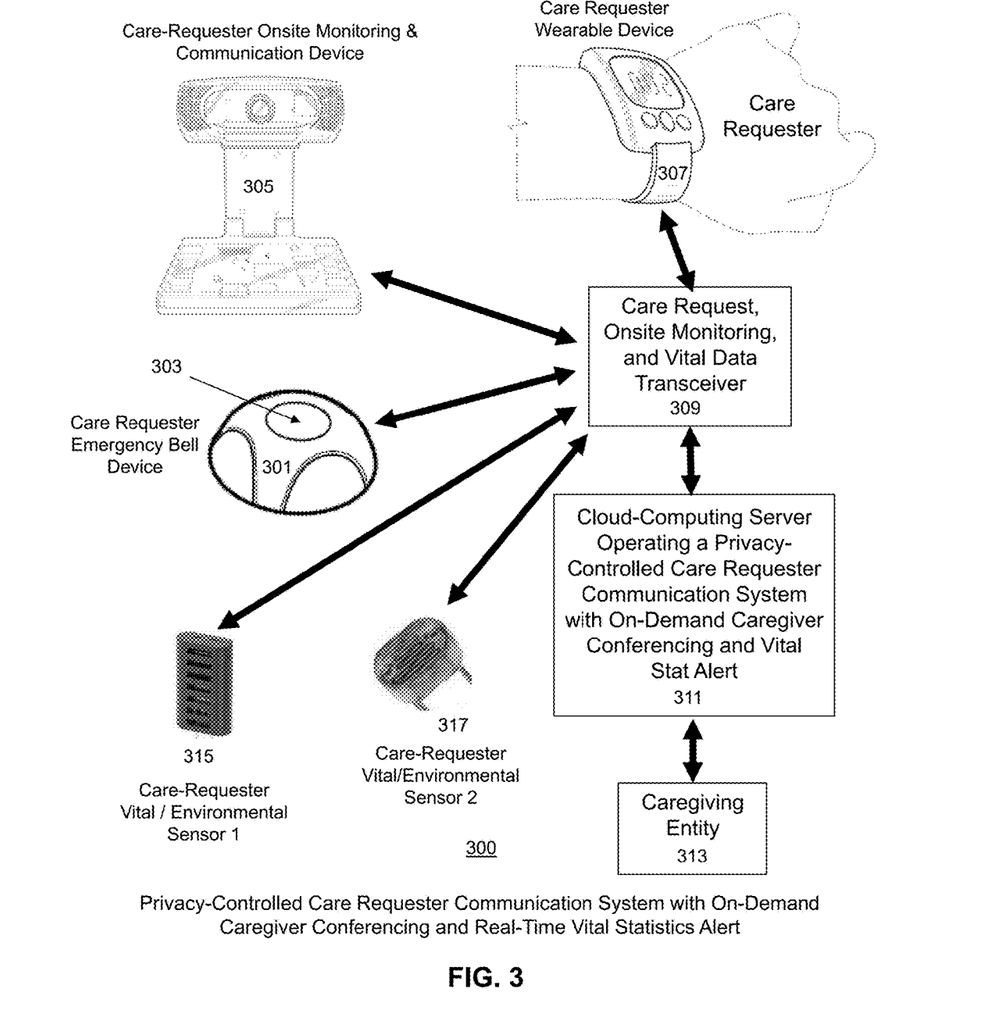
FIG. 3 shows an embodiment of a privacy-controlled care requester communication system with on-demand caregiver conferencing and real-time vital statistics alert, in accordance with an embodiment of the invention.

FIG. 3 shows an embodiment (300) of a privacy-controlled care requester communication system with on-demand caregiver conferencing and real-time vital statistics alert, in accordance with an embodiment of the invention. In a preferred embodiment of the invention, at least one care-requester onsite monitoring and communication device (305) with on-demand caregiver conference and real-time vital statistics alert capabilities is connected to a cloud-computing server operating a care requester communication system (311) via a wireless and/or wired data network and a care request, onsite monitoring, and vital data transceiver (309), as shown in FIG. 3. In some embodiments, a multiple number of care-requester onsite monitoring and communication devices (i.e. 305) for one particular care requester may be installed in various places in a residence or a patient care facility to provide patient monitoring and communication in multiple vantage points for the privacy-controlled care requester communication system.

Furthermore, in the preferred embodiment of the invention, the privacy-controlled care requester communication system may also incorporate a care requester emergency bell device (301) with an emergency bell button (303) and/or a care requester wearable device (307) (e.g. a patient monitoring-specialized watch, an electronic necklace, etc.), which are designed to initiate an emergency alert or a welfare check request from a care requester to a caregiving entity (313) in case of emergency needs. In some embodiments of the invention, the care requester wearable device (307) may also incorporate environmental or vital sensors (e.g. 315, 317) that measure the care requester's vital signs (e.g. heart rates, body temperatures, blood sugar levels, blood pressure, electrocardiogram, etc.) or surrounding environmental parameters (e.g. ambient air temperatures, carbon monoxide levels, humidity, etc.) in real time, which are transmitted to the cloud-computing server (311) for artificial intelligence-based machine analysis of patient health and safety risk determinations in real time.

For example, if the privacy-controlled care requester communication system determines that the current carbon monoxide level is excessively high or the current ambient air temperature is dangerously low for the care requester based machine analysis of real-time environmental sensory values in the care requester's bedroom, the privacy-controlled care requester communication system may generate a safety alert to the caregiving entity (313), who in turn can conduct an emergency welfare check in person or conduct appropriate authorities for additional assistance. Similarly, if the privacy-controlled care requester communication system determines that the care requester's heart rate, body temperature, electrocardiogram data, or blood sugar level is suddenly abnormal based on vital sensory parameters transmitted from one or more vital sensors (e.g. 307, 315, 317), then the system may generate a health risk alert to the caregiving entity (313), who in turn takes appropriate measures for immediate welfare checks or follow-up communications with the care requester.

In one embodiment of the invention, environmental and/or vital sensors (315, 317) may be integrated into at least one of the care-requester onsite monitoring and communication device (305), the care requester wearable device (307), and the care requester emergency bell device (303) to facilitate machine-generated and autonomous artificial intelligence-based efficient, coherent, and automated health and safety risk alert services to the caregiving entity (313). In another embodiment of the invention, environmental and/or vital sensors may be standalone or discrete unit sensors located in the vicinity of the care requester's residence that are configured to communicate with the privacy-controlled care requester communication system via a wireless data network as Internet-of-things (IoT) devices.

Furthermore, in the preferred embodiment of the invention, the care-requester onsite monitoring and communication device (305) enables the care requester or the caregiving entity (313) to initiate, approve, and/or receive videoconferencing or teleconferencing communications for routine or emergency communication attempts between the two parties. Importantly, the care-requester onsite monitoring and communication device (305) also functions as a closed-circuit patient monitoring camera, which is configured to track, monitor, and alert the care requester's welfare on a real-time basis to the caregiving entity (313). Motion sensing, face recognition, and other imaging-detection technologies can further be integrated into visual and audio analysis of real-time multimedia feed monitoring at the cloud computing server (311) as an autonomous welfare check alert condition. For example, if the visual and audio analysis of real-time multimedia feed monitoring conducted by the privacy-controlled care requester communication system does not detect the care requester's presence in the field of view of the care-requester onsite monitoring and communication device (305) for more than a few hours, the system may generate a patient absence alert to the caregiving entity (313) via an automated phone call, a text message, an email, or another form of an electronic alert.

Moreover, in the embodiment (300) of the invention as shown in FIG. 3, the privacy-controlled care requester communication system provides intelligent visual and audio patient (i.e. care requester) monitoring within the constraints of care requester-specified privacy controls. For example, if the care requester does not want to give visual and audio monitoring access to the caregiving entity (313) during his or her legally or financially-sensitive phone call to a financial advisor or an attorney, then the care requester can adjust the privacy settings to exclude visual and audio monitoring by the caregiving entity (313) during the sensitive phone call with the financial advisor or the attorney. Likewise, if the care requester is about to change cloths and does not want the caregiving entity (313) to have access to visual monitoring footage, the care requester may adjust privacy settings or press a hot button, if any, on the care-requester onsite monitoring and communication device (305) to exclude the video monitoring feed transmission while retaining the audio monitoring feed transmission to the cloud-computing server (311), in order to protect his or her privacy during the clothing change.

The care requester may also selectively choose video, audio, environmental, or real-time vital statistics information gathered from the care-requester onsite monitoring and communication device (305) and vital and environmental sensors (315, 317) for privacy filtering in data sharing or blocking decisions, based on the care requester's particular privacy preferences during the course of health and safety monitoring. Preferably, the caregiving entity (313) is still able to initiate video conferencing with the care requester and may also be empowered with privacy setting override privileges, if a particular situation is urgent for the safety of the care requester. In the event of a privacy setting override, it is preferable to implement an automated aural and/or visual message to the care requester via the care-requester onsite monitoring and communication device (305) to indicate transparently that the privacy settings are currently being circumvented due to emergency needs of the care requester.

Figure 4:
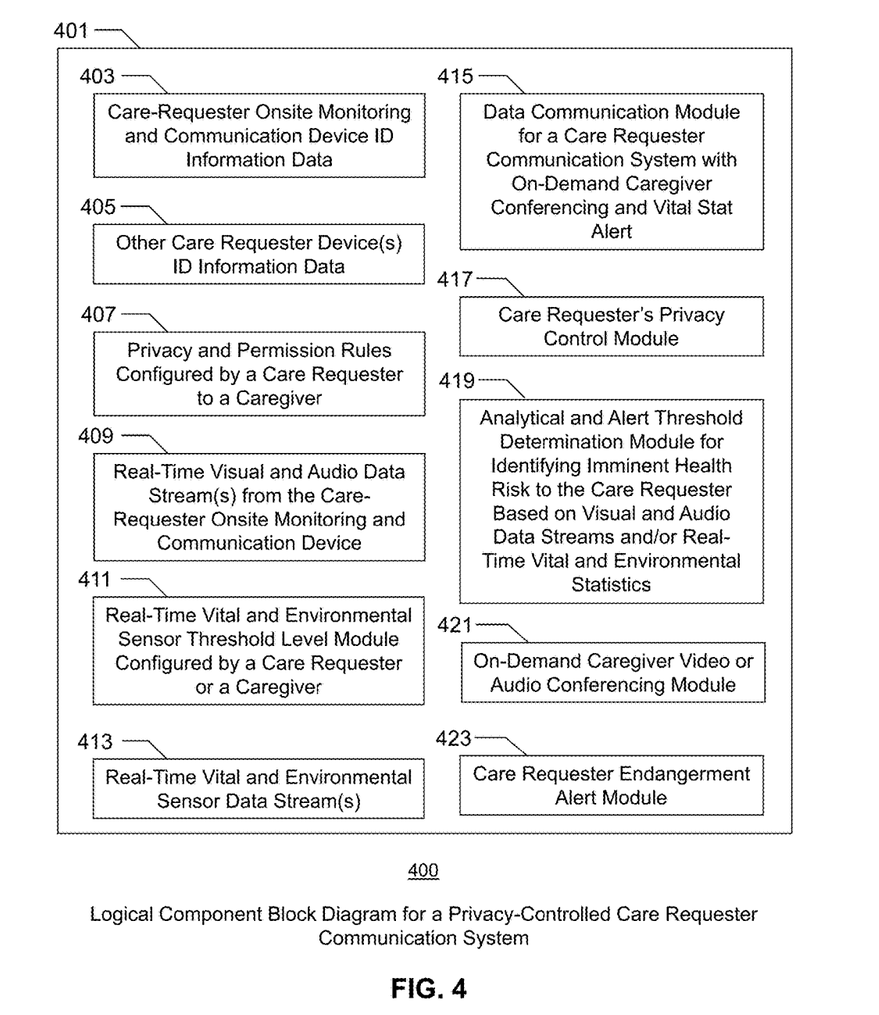
FIG. 4 shows a logical component block diagram for a privacy-controlled care requester communication system with on-demand caregiver conferencing and real-time vital statistics alert, in accordance with an embodiment of the invention.
Figure 5:
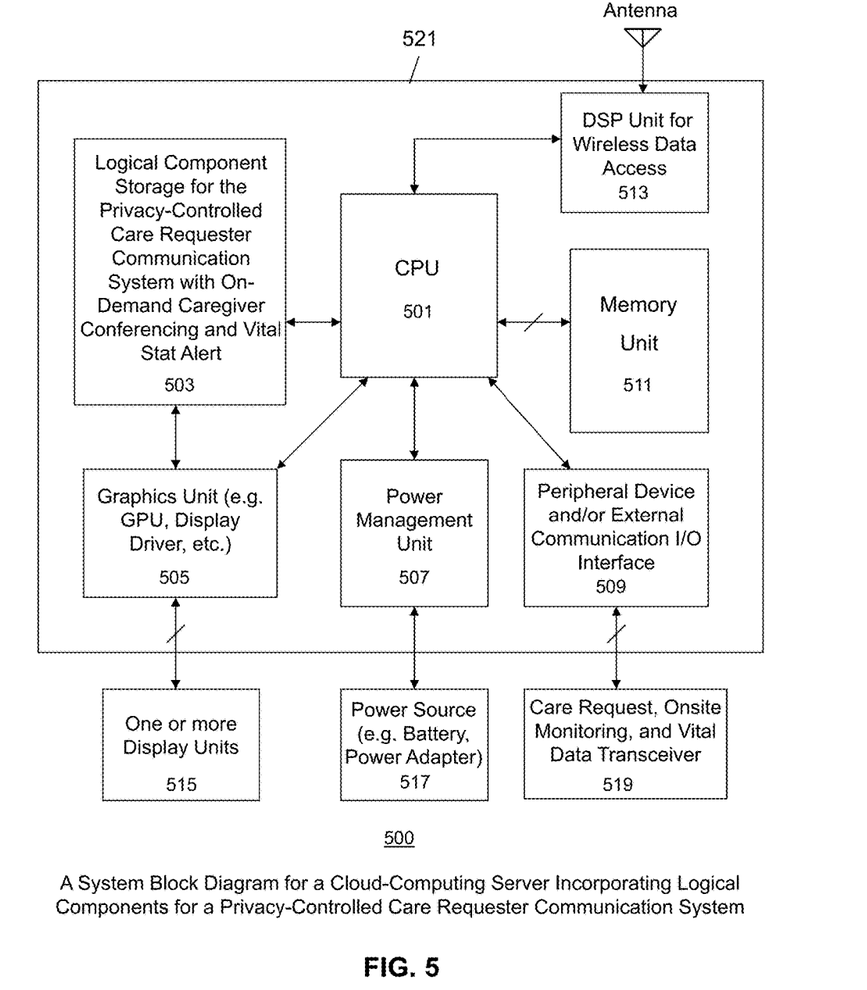
FIG. 5 shows a system block diagram for a cloud-computing server incorporating logical components for a privacy-controlled care requester communication system, in accordance with an embodiment of the invention.

FIG. 4 shows a logical component block diagram (400) for a privacy-controlled care requester communication system with on-demand caregiver conferencing and real-time vital statistics alert, in accordance with an embodiment of the invention. In a preferred embodiment of the invention, one or more logical components (401) of the privacy-controlled care requester communication system are configured to be stored in a data storage (e.g. 213 of FIG. 2, 503 of FIG. 5, etc.) associated with a computer server or hard-coded into an application-specific semiconductor chip, and are also configured to be uploaded to and executed in a memory unit and a CPU of the computer server, as also illustrated in FIG. 5.

Furthermore, in the preferred embodiment of the invention, the logical components (401) of the privacy-controlled care requester communication system comprise a real-time vital and environmental sensor threshold level module (411), a data communication module (415) for a care requester communication system with on-demand caregiver conference and vital stat alert, a care requester's privacy control module (417), an analytical and alert threshold determination module for identifying imminent health risk to the care requester based on visual and audio data streams and/or real-time vital and environmental statistics (419), an on-demand caregiver video or audio conferencing module (421), and a care requester endangerment alert module (423).

The real-time vital and environmental sensor threshold level module (411) provides a sensor alert adjustment user interface to a caregiving entity or to a care requester. For example, the caregiving entity is able to set patient-specific safety and health risk alert threshold values, such as threshold points of potential endangerments associated with the care requester's heart rate, blood pressure, body temperature, ambient air temperature, and ambient carbon monoxide levels, by using a computerized user interface provided by the real-time vital and environmental sensor threshold level module (411).

Furthermore, the care requester's privacy control module (417) is configured to provide a computerized privacy control adjustment user interface to the care requester for various elements of the privacy-controlled care requester communication system, including a care-requester onsite monitoring and communication device, a care requester wearable device, a care requester emergency bell device, a vital sensor, and/or an environmental sensor associated with the privacy-controlled care requester communication system. By providing the computerized privacy control adjustment user interface accessible on a personal computer, a tablet computer, a smart phone, or on a surface of an element of the system itself, the care requester's privacy control module (417) empowers the care requester to configure, select, and adjust personally-comfortable levels of privacy for patient monitoring and communication activities with the caregiving entity. As shown in FIG. 4, the care requester's privacy control module (417) may take privacy and permission rules (407) that have been defined, configured, or adjusted by the care requester as the privacy control rules, which are subsequently enforced by the care requester's privacy control module (417) for the privacy-controlled care requester communication system.

Continuing with the embodiment of the invention as shown in FIG. 4, the analytical and alert threshold determination module (419) for identifying imminent health risk to the care requester is capable of making artificial intelligence-based autonomous decisions (i.e. without manual human monitoring or intervention) for generating health and/or safety risk alerts to a caregiving entity after a dynamic or real-time analysis of visual, audio, and sensory data streams provided by at least one of the care-requester onsite monitoring and communication device, the care requester wearable device, the care requester emergency bell device, the vital sensor, and/or the environmental sensor associated with the privacy-controlled care requester communication system. For example, if the care requester is not identified in visual feeds and not heard in audio feeds for the last three hours, the analytical and alert threshold determination module (419) may determine that a safety alert to the caregiving entity is deemed appropriate. In this example, if the absence of the care requester, as evidenced in visual and audio feeds, also coincides with dangerous or no vital signs from sensory data parameters associated with the care requester, then the analytical and alert threshold determination module (419) may additionally determine that the current situation justifies an urgent emergency alert not only to the caregiving entity, but also to a local emergency service by calling 911 and automatically providing machine-generated verbalized information on behalf of the care requester via an interactive voice response protocol, which in turn initiates an ambulance dispatch.

As shown in the logical component block diagram (400), any safety and health risk alerts, which may be in form of phone calls, text messages, emails, or another method of messaging to the caregiving entity and/or to local emergency authorities, can be queued in and processed by a care requester endangerment alert module (423) incorporated in one of the system devices (e.g. 301, 305, 307 in FIG. 3) or in the cloud-computing server (e.g. 311 in FIG. 3).

Furthermore, the logical components for the privacy-controlled care requester communication system also include the on-demand caregiver video or audio conferencing module (421) that enables the caregiving entity or the care requester to initiate, approve, or receive videoconferencing or audio conferencing through a care-requester onsite monitoring and communication device, a care requester wearable device, or a care requester emergency bell device. The on-demand video or audio conferencing may be requested between the caregiving entity and the care requester on a routine or emergency basis via a wireless data and/or a cellular network, even when the care requester does not have a cellular phone, a telephone, or another conventional communication device readily available. In addition, the data communication module (415) in the logical components of the privacy-controlled care requester communication system enables various elements of the system to transmit and receive visual, audio, textual, sensory, and other digitized datasets via at least one of wireless, cellular, and satellite data networks for seamless operation.

Moreover, the logical components for the privacy-controlled care requester communication system also include care-requester onsite monitoring and communication device ID information (403) and other care requester device ID information (405), each of which uniquely identifies a device element connected to the privacy-controlled care requester communication system. Furthermore, as shown in the logical component block diagram (400), the logical components may also receive, relay, and/or process real-time vital and environmental data streams (413) from vital and environmental sensor devices for subsequent sensory data analysis conducted by the analytical and alert threshold determination module (419) for identifying imminent health risk to the care requester.

FIG. 5 shows a system block diagram (500) for a cloud-computing server incorporating logical components (e.g. 401 of FIG. 4) for a privacy-controlled care requester communication system, in accordance with an embodiment of the invention. In a preferred embodiment of the invention, the cloud-computing server incorporates a logical component storage (503) for one or more components of the privacy-controlled care requester communication system to enable on-demand caregiver conferencing and vital stat alert capabilities. The logical component storage (503) may contain one or more logical components that were previously described in FIG. 4.

In the preferred embodiment of the invention, the cloud-computing server for the privacy-controlled care request communication system comprises a CPU (501) and a memory unit (511), which are configured to execute and process a plurality of computerized instructions and visual, audio, and sensory data received from various elements of the privacy-controlled care request communication system. Moreover, the cloud-computing server for the privacy-controlled care request communication system also includes a graphics unit (505) (e.g. a graphics processor, a display driver, and etc.), a power management unit (507), a peripheral device and/or external communication I/O interface (509), and a digital signal processing (DSP) unit for wireless data access (513). These logical units may be placed on a single printed circuit board in one embodiment of the invention, or on a plurality of printed circuit boards in another embodiment of the invention.

Furthermore, in the preferred embodiment of the invention, the CPU (501) is configured to control each logical unit operatively (i.e. directly or indirectly) connected to the CPU (501). The memory unit (511) typically comprises volatile memory banks based on DRAM's. In some embodiments of the invention, the memory unit (511) may use non-volatile memory technologies such as SRAM's and/or Flash memory. The memory unit (511) is capable of storing or uploading programs and applications which can be executed by the CPU (501), the graphics unit (505), or another logical unit operatively connected to the memory unit (511). In particular, in the preferred embodiment of the invention, software-implemented components of the privacy-controlled care request communication system may be stored in a local or cloud data storage unit and executed on the CPU (501) and the memory unit (511) of the cloud-computing server as needed.

In addition, as shown in FIG. 5, the digital signal processing (DSP) unit (513) for wireless data access is operatively connected to an radio frequency (RF) antenna. The digital signal processing (DSP) unit (513) for wireless data access is generally configured to receive and transmit data packets for visual, audio, sensory, and device control information among various elements of the privacy-controlled care requester communication system. The DSP unit (513) can also communicate with other devices or other cloud-computing resources in a local area network and the Internet. Moreover, the power management unit (507) is operatively connected to a power supply unit and a power source (e.g. battery, power adapter) (517), and the power management unit (507) generally controls power supplied to various logical units in the cloud-computing server (521). Furthermore, the peripheral device and/or external communication I/O interface (509), as shown in FIG. 5, can be operatively connected to a plurality of system elements and peripheral devices through a care request, onsite monitoring, and vital data transceiver (519).

Continuing with the system block diagram (500) in FIG. 5, the graphics unit (505) for the cloud-computing server (521) comprises a graphics processor, a display driver, a dedicated graphics memory unit, and/or another graphics-related logical components. In general, the graphics unit (505) is able to process and communicate graphics-related data with the CPU (501), the display driver, and/or the dedicated graphics memory unit. The graphics unit (505) is also operatively connected to one or more display units (515).

Figure 6:
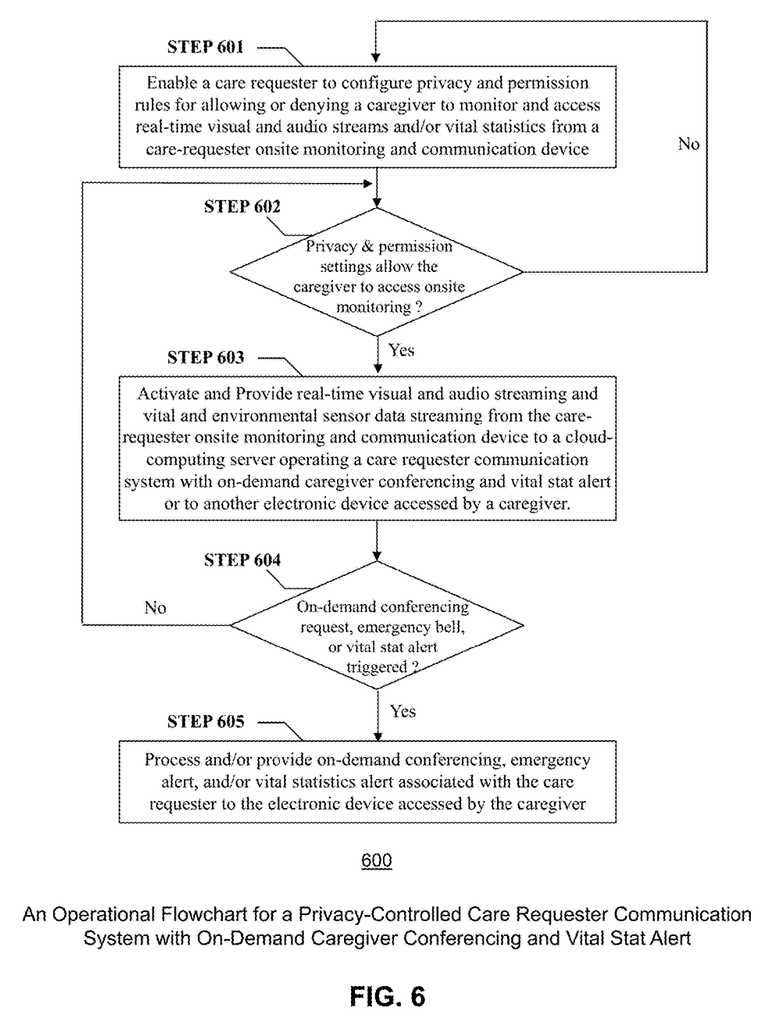
FIG. 6 shows an operational flowchart for a privacy-controlled care requester communication system with on-demand caregiver conferencing and vital stat alert, in accordance with an embodiment of the invention.

FIG. 6 shows an operational flowchart (600) for a privacy-controlled care requester communication system with on-demand caregiver conferencing and vital stat alert, in accordance with an embodiment of the invention. As shown in STEP 601, the privacy-controlled care requester communication system first enables a care requester to configure privacy and permission rules, which allow or deny a caregiver to monitor and access real-time visual and audio streams, vital statistics, and environmental variables from a care-requester onsite monitoring and communication device.

If the current privacy and permission settings of the privacy-controlled care requester communication system allow the caregiver to access onsite monitoring, as shown in STEP 602, then the privacy-controlled care requester communication system activates and/or provides real-time visual and audio streaming as well as vital and environmental sensory data streaming from the care-requester onsite monitoring and communication device to a cloud computing server that operates a care requester communication system, as shown in STEP 603. The real-time visual, audio, and sensory information may also be transmitted to another electronic device accessed by a caregiver, if the privacy and permissions settings allow such information transfer.

Subsequently, the privacy-controlled care requester communication system continues to generate, transmit, analyze, and store the real-time visual, audio, and sensory information associated with the care requester without interruption until an on-demand conferencing request, an emergency bell, a health risk alert, or a safety alert is triggered by the privacy-controlled care requester communication system, as shown in STEP 604. If any of the conferencing requests, bells, or alerts are triggered, the privacy-controlled care requester communication system processes and/or provides on-demand conferencing, emergency alerts, and/or vital statistics alerts associated with the care requester to the electronic device accessed by the caregiver, as shown in STEP 605.

Various embodiments of the present invention provide several key advantages to conventional methods of senior citizen and patient monitoring. For instance, one advantage of an embodiment of the present invention is providing a novel privacy-controlled care requester communication system that accommodates privacy level-adjustable onsite monitoring as well as two-way communication capabilities between a care requester and a caregiver. Another advantage of an embodiment of the present invention is providing a novel privacy-controlled care requester communication system that incorporates a dedicated onsite monitoring device that incorporates dual functionalities of privacy level-adjustable patient security monitoring and on-demand video or audio conferencing.

In addition, another advantage of an embodiment of the present invention is providing a privacy-controlled care requester communication system that also incorporates one or more emergency bell devices, patient vital sensors, environmental sensors, and patient-wearable devices, which enable the privacy-controlled care requester communication system to produce autonomous machine-generated decisions in creating patient endangerment alerts to electronic devices accessed by caregivers for efficient and timely patient care management. Furthermore, another advantage of an embodiment of the present invention is providing a method of operating a privacy-controlled care requester communication system that enables remote yet timely and proactive monitoring of care requesters who may encounter sudden health or safety endangerments.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A privacy-controlled care requester communication system comprising:
    a care-requester onsite monitoring and communication device that provides dual capabilities of a closed-circuit visual and audio monitoring of a care requester and an on-demand welfare check videoconferencing initiated by a caregiving entity;
    a cloud-computing server incorporating a care requester's privacy control module that enables creations and modifications of the care requester's preferred privacy and permissions rules not for a past health record, but for a planned future event organized by the care requester for a future timeslot that requires a temporary and timed exclusion from the closed-circuit visual and audio monitoring of the care requester, when the planned future event participated by the care requester occurs in the future timeslot, an analytical and alert threshold determination module for identifying imminent health risk to the care requester from the closed-circuit visual and audio monitoring, an on-demand welfare check videoconferencing module, and a care requester endangerment alert module, which are executed in a CPU and a memory unit of the cloud-computing server to operate the privacy-controlled care requester communication system, wherein the imminent health risk identified by the analytical and alert threshold determination module empowers the caregiving entity to override the care requester's preferred privacy and permissions rules even during the temporary and timed exclusion to resume the closed-circuit visual and audio monitoring of the care requester and to initiate the on-demand welfare check videoconferencing by the caregiving entity;
    a care requester's privacy control and permission rules interface generated by the care requester's privacy control module, which assists the creations and the modifications of the care requester's preferred privacy and permissions rules for the planned future event in the future timeslot to grant or deny the caregiving entity a transmission or access privilege to the closed-circuit visual and audio monitoring during the planned future event in the future timeslot for a care requester-configured future privacy scheduling and enforcement; and
    a data network operatively connecting the care-requester onsite monitoring and communication device and the cloud-computing server incorporating the care requester's privacy control module, the analytical and alert threshold determination module for identifying the imminent health risk to the care requester from the closed-circuit visual and audio monitoring, the on-demand welfare check videoconferencing module, and the care requester endangerment alert module.

2. The privacy-controlled care requester communication system of claim 1, further comprising at least one of an environmental sensor and a vital sensor, wherein the environmental sensor measures ambient air temperature, airborne microparticle levels, or airborne carbon monoxide levels, and wherein the vital sensor measures the care requester's heart rate, body temperature, electrocardiogram, blood sugar level, or blood pressure.

3. The privacy-controlled care requester communication system of claim 1, further comprising at least one of a care requester wearable device and a care requester emergency bell device with an emergency bell button, wherein the care requester wearable device and the care requester emergency bell device empower the care requester to initiate a health or safety emergency alert to the caregiving entity via the cloud-computing server and the data network.

4. The privacy-controlled care requester communication system of claim 1, further comprising a care request, onsite monitoring, and vital data transceiver, which operatively connects the care-requester onsite monitoring and communication device, the cloud-computing server, and the data network by enabling transmission or reception of data packets between the care-requester onsite monitoring and communication device and the cloud-computing server.

5. The privacy-controlled care requester communication system of claim 1, wherein the analytical and alert threshold determination module for identifying the imminent health risk to the care requester from the closed-circuit visual and audio monitoring utilizes autonomous artificial intelligence without necessitating a manual human intervention in the cloud-computing server to determine a potential health risk or a potential safety risk to the care requester, which is subsequently forwarded to the care requester endangerment alert module.

6. The privacy-controlled care requester communication system of claim 5, wherein the care requester endangerment alert module creates and transmits a machine-generated voice phone call alert, a text alert, or an email alert to an electronic device accessed by the caregiving entity or by a local emergency care authority to notify an urgent health or safety risk experienced by the care requester.

7. The privacy-controlled care requester communication system of claim 3, wherein the care requester wearable device is an electronic watch or an electronic necklace that also incorporates an environmental sensor or a vital sensor to measure and determine environmental variables or vital signs in real time.

8. The privacy-controlled care requester communication system of claim 4, wherein the care request, onsite monitoring, and vital data transceiver is capable of acquiring, demodulating, and processing wireless data signals from the care-requester onsite monitoring and communication device and the cloud-computing server.

9. The privacy-controlled care requester communication system of claim 1, further comprising a digital signal processing (DSP) unit for wireless data access.

10. The privacy-controlled care requester communication system of claim 1, further comprising a power management unit and an electrical power source.

11. The privacy-controlled care requester communication system of claim 1, further comprising a graphics unit and one or more display units.

12. The privacy-controlled care requester communication system of claim 1, wherein the on-demand welfare check videoconferencing module provides a routine or emergency videoconferencing or teleconferencing between the care requester and the caregiving entity.

\* \* \* \* \*